United States Patent [19]

Grundei et al.

[11] Patent Number: 5,048,509

[45] Date of Patent: Sep. 17, 1991

[54] CERVICAL SUPPORT

[75] Inventors: Jaana Grundei, Lübeck; Andreas Timmermann, Ekelsdorf, both of Fed. Rep. of Germany

[73] Assignee: Adev Gesellschaft fur Entwicklung und Vertrieb von Medizintechnischen Artikeln mbH, Lübeck, Fed. Rep. of Germany

[21] Appl. No.: 478,354

[22] Filed: Feb. 12, 1990

[30] Foreign Application Priority Data

Feb. 28, 1989 [DE] Fed. Rep. of Germany ....... 3906233

[51] Int. Cl.⁵ .......................... A61H 1/02; A61F 5/04
[52] U.S. Cl. .................................. 128/75; 128/87 B; 128/DIG. 23; 128/DIG. 15
[58] Field of Search ................. 128/87 R, 87 B, 76 R, 128/164, DIG. 23, DIG. 15

[56] References Cited

U.S. PATENT DOCUMENTS

| | | | |
|---|---|---|---|
| 1,473,506 | 11/1923 | Nessler | 128/DIG. 23 |
| 3,320,950 | 5/1967 | McElvenny | 128/75 |
| 3,477,425 | 11/1969 | Grassal | 128/75 |
| 3,530,853 | 9/1970 | Bond | 128/87 B |
| 3,696,810 | 10/1972 | Gaylord, Jr. | 128/75 |
| 3,756,226 | 9/1973 | Calabrese | 128/75 |
| 3,850,164 | 11/1974 | Hare | 128/75 |
| 3,964,474 | 6/1976 | Fox | 128/87 B |
| 4,205,667 | 6/1980 | Gaylord, Jr. | 128/DIG. 23 |
| 4,232,663 | 11/1980 | Newton | 128/DIG. 23 |

*Primary Examiner*—Robert A. Hafer
*Assistant Examiner*—Michael Brown
*Attorney, Agent, or Firm*—Dvorak and Traub

[57] ABSTRACT

A cervical support has an inherently stable support body of elastic foam material, provided with a covering of textile material, the free ends of which body overlap each other at the rear in a nape support region of the cervical support and can be detachably connected to each other. The nape support region is of greater height than a front, chin support region of the cervical support. For improved fit against the patient's body, and the relief of pressure thereagainst, the nape support region follows a path which is substantially partially circular or partially elliptical, and merges into jaw support regions which extend symmetrically and in mirror image relationship with respect to an imaginary longitudinal axis connecting the centers of the nape support region and the chin support region. Each jaw support region is of flat S-shape, which at a certain distance from the chin support region, is bowed towards the longitudinal axis.

14 Claims, 4 Drawing Sheets

CERVICAL SUPPORT

FIELD OF THE INVENTION

This invention relates to a cervical support, provided by a substantially inherently stable support body of elastic foam material, which may be provided with a covering of textile material, and which can be placed about the neck of a patient to wear it. Free ends of the body overlap each other at the rear thereof in a nape support region of the body and are detachably connectable with each other. The height of the nape support region is greater than that of a chin support forward region of the support body opposite to the nape support region. Two lateral jaw support regions of the body have upper and lower marginal contours adapted to the anatomical shape of the chin, and of the area of the patient's body proximate to the neck, respectively.

BACKGROUND OF THE INVENTION

Such a cervical support, which is described in the DE-A-24 04 683, has proved to be successful in practice. It has been found, however, that some support regions of the cervical support, in particular at the front neck region thereof, need to be improved in order to reduce, or to prevent exertion of pressure at said regions against parts of the patient's body engaged by the cervical support.

SUMMARY OF THE INVENTION

It is an object of the present invention to provide a cervical support which affords the required immobilization of the patient's cervical vertebral column, complies with the wearer's anatomy, can be rapidly secured about the patient's neck and can be worn with improved comfort for the patient.

A cervical support, according to the present invention, is provided by a substantially inherently stable support body of elastic foam material, which may optionally be provided with a covering of textile material, and which can be placed around the neck of the patient, the free ends of which body overlap each other to the rear at the nape support region and are detachably connectable with each other, the height of the nape support region being greater than the height of the front chin support region of the support body, lying opposite thereto. Two lateral jaw support regions are adapted with regard to their upper and lower marginal contours to the anatomical shape of the chin or respectively the area of the body proximate to the neck. In each case seen in top view, the nape support region follows a path which is substantially partially circular or partially elliptical in shape, and merges at an imaginary major transverse axis, into the jaw support regions, which, in relation to an imaginary longitudinal axis connecting the centers of the nape support region and the chin support region and running vertically with respect to the major transverse axis, extend symmetrically in mirror image relationship and in each case have a flat elongate S-shape with an arc directed inwards towards the longitudinal axis in the region of a further imaginary minor transverse axis extending parallel to the major transverse axis and at a distance therefrom. The chin support region follows a path substantially in the shape of a partial circle.

Preferably, the length of said major transverse axis is approximately 0.80 to 0.95 of the length of said longitudinal axis, the length of said minor transverse axis being approximately 0.5 to 0.7 of the length of said longitudinal axis, said major and minor transverse axes being spaced from each other by a distance of 0.35 to 0.45 of the length of said longitudinal axis.

The nape support region of the cervical support is preferably formed with an upper marginal recess, the bottom of which lies below the level of the laterally adjoining parts of the nape support region. The lower edge of the nape support region preferably extends below that of said chin support region.

The cervical support according to the invention fits the patient to an improved extent and thus provides improved comfort for the patient, especially where the cervical support must be worn for a lengthy period of time, and also affords the needed immobilization of the cervical vertebral column. By virtue of the non-oval circumferential shape of the cervical support, and by virtue of the improved arrangement of the upper and lower circumferential edges of the cervical support, it is supported by additional areas of the patient's body for better distribution of the load on the patient's body, this being of especially beneficial effect in respect of the front region of the neck, the occiput region and the region of the patient's back proximate to the neck. Also, the freedom of movement of the patient's head is improved without impairing the immobilization of the cervical vertebral column.

The above features enable an expanded field of use for the cervical support, for example in the case of new bone fractures and tumors of the column and the cervical support may be worn by patients with protruding skeletal parts within the effective range of the cervical support.

DETAILED DESCRIPTION OF THE INVENTION

Figure 1:
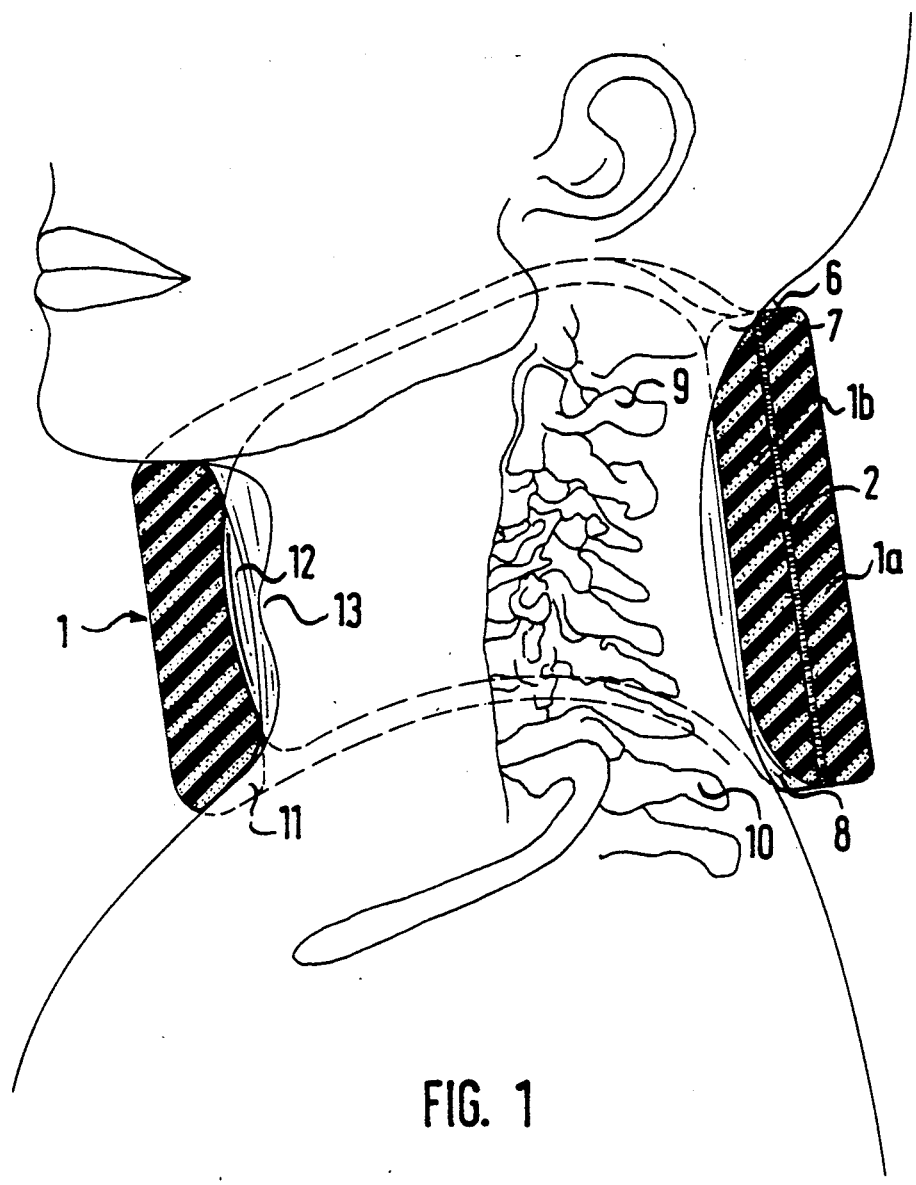
FIG. 1 is a vertical sectional view of a cervical support according to an embodiment of the invention, in place about the neck of a patient.
Figure 2:
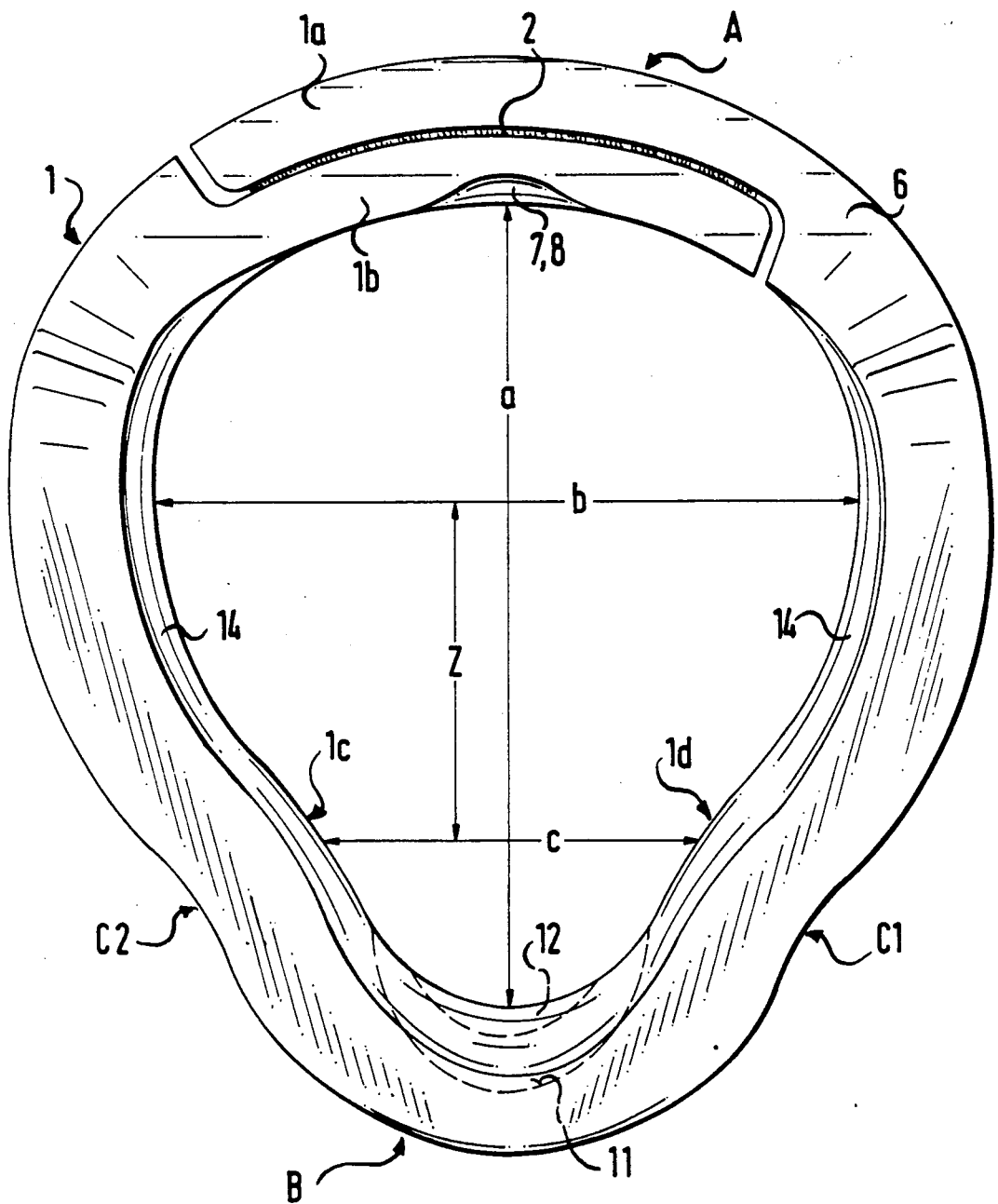
FIG. 2 is a top plan view of the cervical support drawn to a larger scale than FIG. 1.

The cervical support comprises a flexible and inherently stable support body 1 made of an elastic foam material and which when in use lies closely against the neck of the wearer as shown in FIG. 1. The body 1 is secured about the neck of the patient wearing the cervical support by means of overlapping end pieces 1a and 1b which are secured together by means of burred closure surfaces 2 thereon (FIG. 2), in the region of the nape of the patient's neck. When the cervical support is not in use, the pieces 1a and 1b are secured together by means of the closure surfaces 2, as shown in FIG. 2 so that the support is closed and so forms a circumferentially stable body, which can be opened out for use and is self-closing.

Figure 3:
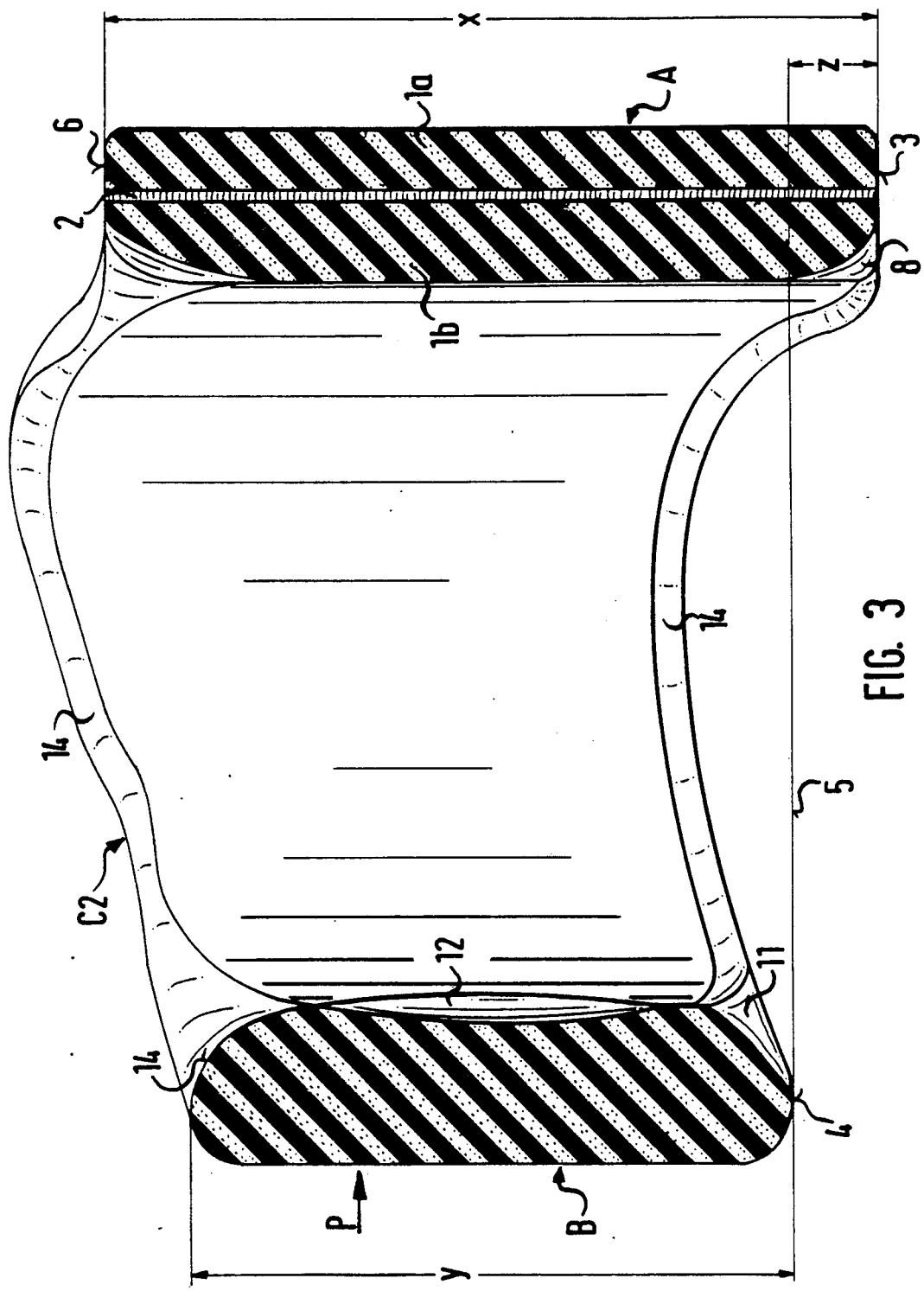
FIG. 3 is a vertical sectional view of the cervical support drawn to a larger scale than FIG. 1.

The upper and lower circumferential edges of the body 1 are adapted to the anatomical conditions of the head and shoulder regions, respectively, adjoining the wearer's neck. To this end, the nape support region A of the body 1 is of greater height than its chin support region B. As shown in FIG. 3, the height X of the nape support region A exceeds by approximately 1.15 to 1.70, and preferably 1.15 to 1.40, the height Y of the chin support region B. Also, the lower edge 3 of the nape support region A lies below the lower edge 4 of the chin support region B, by a distance Z which is approximately 0.15 to 0.25 and preferably 0.18 to 0.22 of the height X of the nape support region A. A tangent 5 selected as a reference line for the distance Z, touches the lower edge 4 of the chin support region B, the distance Z extending therebelow. By virtue of the extra downward extent, that is to say the distance Z, of the region A the cervical support sits lower on the patient so that the distribution of pressure against the patient's body is such that the cervical support is more comfortable to wear than if the nape support region A did not extend below the chin support region B. In order to improve the fit of the cervical support against the patient's neck the support has the improved circumferential shape shown in FIG. 2, the nape support region A extending along a partially elliptical path up to a first imaginary transverse axis b. Alternatively, the path extending up to the axis b may be in the form of part of a circle. Two opposite jaw support regions C1 and C2 adjoining the nape support region A on a either side of an imaginary longitudinal axis a extending centrally through the regions A and B, are symmetrical with respect to the axis a and are disposed in mirror image relationship with one another. The jaw support regions C1 and C2 describe inwardly directed arcs 1c and 1d, the interior apices of which lie proximate to a further imaginary transverse axis c extending parallel to the axis b. As shown in FIG. 2, the chin support region B describes approximately an arc of a circle.

The length of the axis a being selected as a reference valve, the length of the axis b is approximately 0.80 to 0.95 of the length of the axis a, the length of the transverse axis c being approximately 0.5 to 0.7 of the length of the axis a. The transverse axes b and c are spaced from each other by a distance Z which corresponds to 0.35 to 0.45 of the length of the axis a, and are perpendicular thereto.

The substantially flattened elongate S-shape of the jaw support regions C1 and C2, enables improved support of the cervical vertebral column in the front region of the neck.

As best seen in FIG. 3, the upper edge of the nape support region A is, for further improvement of the cervical support, lowered to the extent that reaction pressure of the cervical support against the tuberosity of the occipital bone is reduced or avoided. Such lower positioning of the upper edge of the nape support region A is of such extent as to produce a marked recess 6 the bottom of which lies below the edges of the lateral parts of the nape support region A. Although the whole bottom of the recess 6 is preferable as low as shown in FIG. 3, the recess 6 may be provided only in the inner one 1b of the end pieces 1a and 1b. Also, the recess can be provided in both of those pieces, the bottom of the recess in the outer piece 1a lying above that of the recess in the part 1b.

Figure 4:
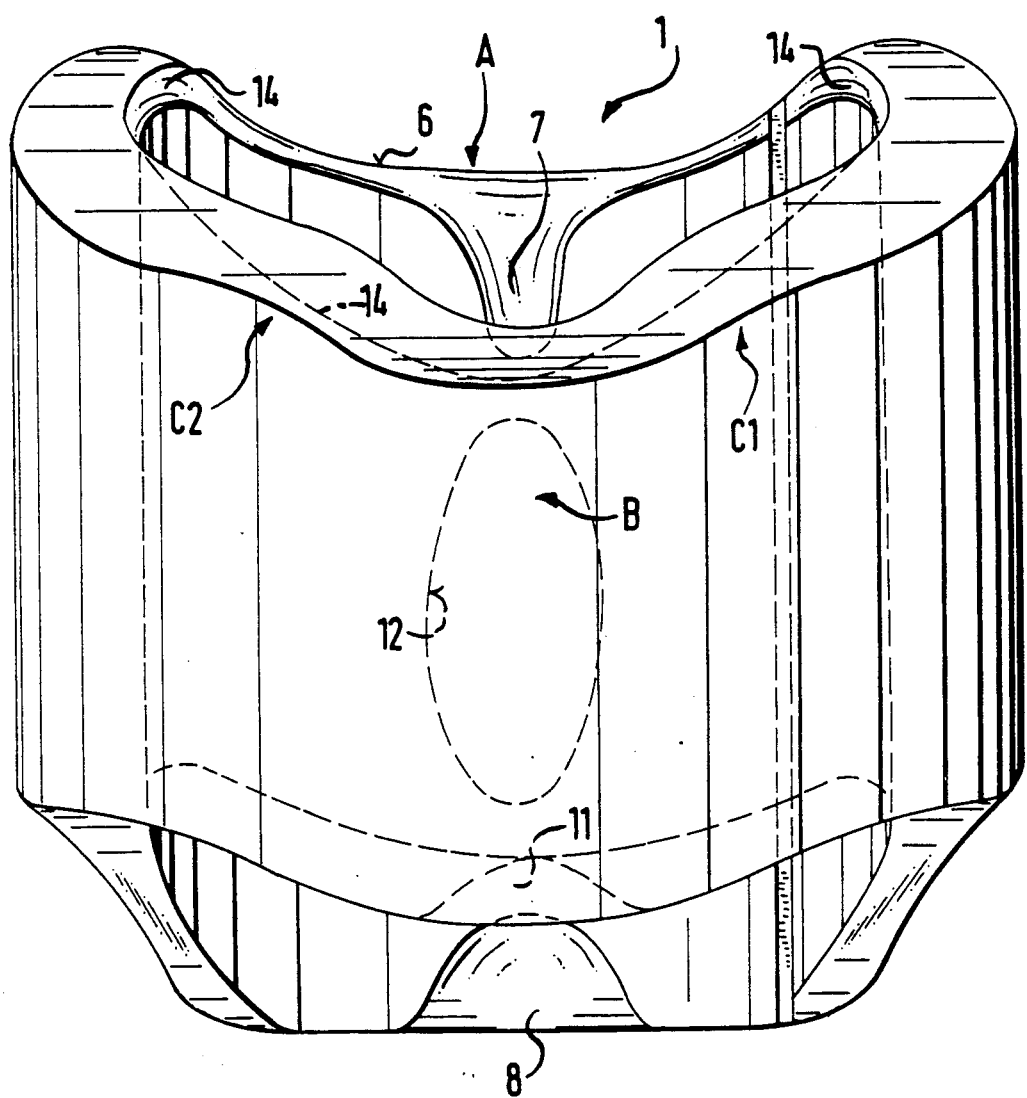
FIG. 4 is a front view of the cervical support taken in the direction of the arrow P in FIG. 3, drawn to a larger scale than FIG. 1.

Also, the end piece 1b provided with clearances 7 and 8 in its upper and lower ends, in the region of the longitudinal center of the cervical support, that is to say on opposite sides of the axis a, as will best be apparent from FIG. 4. The clearances 7 and 8 are in the form of short chamfers opening towards the inner edges of the piece 1b for the alleviation of pressure on the uppermost cervical vertebra 9 and the uppermost thoracic vertebra 10 (FIG. 1), in the case of some patients.

Similarly, the bottom front edge of the chin support region B is provided with an inner central indentation 11 for the reduction of, or the avoidance of, pressure on the upper end of the sternum/clavicle joints.

Also, the chin support region B has disposed centrally of its inner side an approximately oval-shaped depression 12 providing clearance for the patient's larynx 13, as best seen in FIG. 1.

For improved fitting against the patient's body, the upper and lower edges of the cervical support, which are in any event rounded, are more greatly relieved on its inner side and substantially over its entire circumference as shown at 14 in FIG. 3, relief against pressure from the rim region of the cervical support being thereby provided.

The body 1, which consists of a flexible foam material as mentioned above, has a protective covering (not shown) of a textile or a plastics material. The burred closure surfaces 2 enable the cervical support to be adjusted to the diameter of the patient's neck; although other closure means may be used.

In producing the cervical support, the support body 1 is cut out from a block of foam material, in which cuts are made along the inner and outer circumferential walls of the body 1 to be produced. The upper and the lower circumferential edges of the body 1 are similarly produced. The body 1 may alternatively be produced by molding the foam material. The stable support body is then provided with the said covering.

What is claimed is:

1. A cervical support provided by a substantially stable support body of elastic foam material, for encircling the neck of the wearer, the cervical support comprising:

a rearward nape support region having free end pieces which are detachably connectable to each other in overlapping relationship to secure the cervical support about the wearer's neck;

a forward, chin support region opposite to said nape support region and being of smaller height than said nape region; and two lateral, opposed jaw support regions between said nape region and said chin support region and having upper and lower marginal contours configured to the anatomical shape of the chin, and of the wearer's body area proximate to the neck, respectively;

wherein as seen from above the surgical support, the nape support region is of bowed shape and merges on a major transverse axis of said body with said jaw support regions, which are arranged in mirror image, symmetrical, relationship with each other on either side of a longitudinal axis bisecting said nape and chin support regions and extending at right angles to said major transverse axis, each jaw support region defining an arc projecting inwardly of said body proximate to a minor transverse axis thereof parallel to said major transverse axis and being spaced therefrom, said chin support region substantially defining an arc of a circle, and wherein the length of said major transverse axis is approximately 0.80 to 0.95 of the length of said longitudinal axis, the length of said minor transverse axis being approximately 0.5 to 0.7 of the length of said longitudinal axis.

2. A cervical support as claimed in claim 1, wherein said major and minor transverse axes are spaced from each other by a distance of 0.35 to 0.45 of the length of said longitudinal axis.

3. A cervical support as claimed in claim 1, wherein said major and minor transverse axes are spaced from one another by a distance of 0.40 to 0.43 of the length of said longitudinal axis.

4. A cervical support as claimed in claim 1, wherein the height of said nape support region is greater than that of said chin support region by a ratio of 1.15 to 1.40.

5. A cervical support as claimed in claim 1, wherein the nape support region extends below the chin support region by between 0.15 to 0.25 of the height of the nape support region.

6. A cervical support as claimed in claim 1, wherein the nape support region extends below the chin support region by between 0.18 to 0.22 of the height of the nape support region.

7. A cervical support as claimed in claim 1, wherein a marginal recess is provided in the top of the nape support region, the bottom of said recess lying below laterally adjoining parts of the nape region.

8. A cervical support as claimed in claim 7, wherein said recess is provided in one of said free end pieces which lies inwardly of said body, the upper edge of the other free end piece lying above the recess.

9. A cervical support as claimed in claim 1, wherein an indentation is provided in the lower edge of the chin support region.

10. A cervical support as claimed in claim 1, wherein a depression for larynx clearance is provided in the chin support region on its inner side.

11. A cervical support as claimed in claim 1, wherein a central clearance recess is provided in each of the upper and lower ends of the nape support region on the inner side of the nape support region.

12. A cervical support as claimed in claim 1, wherein as seen from above the cervical support, said nape region is of partially circular shape.

13. A cervical support as claimed in claim 1, wherein as seen from above the cervical support, said nape region is of partially elliptical shape.

14. A cervical support as claimed in claim 1, wherein said support body is provided with a textile cover.

* * * * *